(12) United States Patent
Oba et al.

(10) Patent No.: US 9,976,934 B2
(45) Date of Patent: May 22, 2018

(54) SENSOR

(71) Applicant: NGK Spark Plug Co., LTD., Nagoya (JP)

(72) Inventors: Takehiro Oba, Kounan (JP); Yuichi Yamada, Komaki (JP); Kunihiko Yonezu, Inuyama (JP)

(73) Assignee: NGK SPARK PLUG CO., LTD., Nagoya (JP)

( * ) Notice: Subject to any disclaimer, the term of this patent is extended or adjusted under 35 U.S.C. 154(b) by 308 days.

(21) Appl. No.: 14/991,572

(22) Filed: Jan. 8, 2016

(65) Prior Publication Data

US 2016/0202144 A1 Jul. 14, 2016

(30) Foreign Application Priority Data

Jan. 9, 2015 (JP) ................................. 2015-002895

(51) Int. Cl.
| | |
|---|---|
| *G01M 15/02* | (2006.01) |
| *F02D 41/14* | (2006.01) |
| *G01N 27/409* | (2006.01) |
| *G01N 27/41* | (2006.01) |
| *G01N 27/407* | (2006.01) |

(52) U.S. Cl.
CPC ......... *G01M 15/02* (2013.01); *F02D 41/1454* (2013.01); *G01N 27/407* (2013.01); *G01N 27/409* (2013.01); *G01N 27/41* (2013.01)

(58) Field of Classification Search
CPC .... G01N 27/407; G01N 27/409; G01N 27/41; F02D 41/1454; G01K 2205/04
See application file for complete search history.

(56) References Cited

U.S. PATENT DOCUMENTS 7,222,516 B2 * 5/2007 Nishio ............... G01N 27/4062
73/23.31
8,702,934 B2 * 4/2014 Tsuzuki ............... G01N 27/407
123/703

(Continued)

FOREIGN PATENT DOCUMENTS

| JP | 2002-296220 A | 10/2002 |
| JP | 2007-71582 A | 3/2007 |
| JP | 2008-298731 A | 12/2008 |

OTHER PUBLICATIONS

Office Action dated Jan. 30, 2018 for the corresponding Japanese Patent Application No. 2015-002895.

*Primary Examiner* — Freddie Kirkland, III
(74) *Attorney, Agent, or Firm* — Leason Ellis LLP

(57) ABSTRACT

A sensor includes: a detection element; a separator including an insertion portion into which a rear side of the detection element is inserted, and a plurality of terminal housing portions that are disposed surrounding a circumference of the insertion portion around an axial direction, and extend in the axial direction; and a connection terminal that is electrically connected to an electrical connection terminal portion to form a current path. The connection terminal includes a frame body portion and an element contact portion. The sensor further includes a first regulation portion that is located at a position closer to the detection element relative to the frame body portion, in a direction in which a first main surface and a second main surface oppose each other, and regulates the movement of the frame body portion in a direction approaching the detection element.

9 Claims, 11 Drawing Sheets

(56) References Cited

U.S. PATENT DOCUMENTS

| | | | |
|---|---|---|---|
| 9,322,680 B2* | 4/2016 | Yonezu | G01N 27/4078 |
| 9,360,448 B2* | 6/2016 | Yonezu | G01N 27/407 |
| 9,581,565 B2* | 2/2017 | Kume | G01M 15/102 |
| 2008/0295576 A1 | 12/2008 | Yamauchi | |
| 2009/0200164 A1* | 8/2009 | Yoshikawa | G01N 27/4062 |
| | | | 204/406 |

* cited by examiner

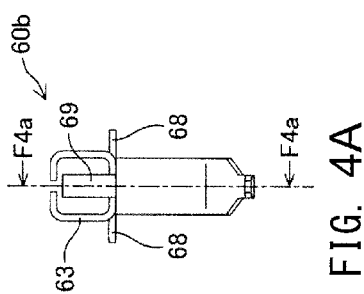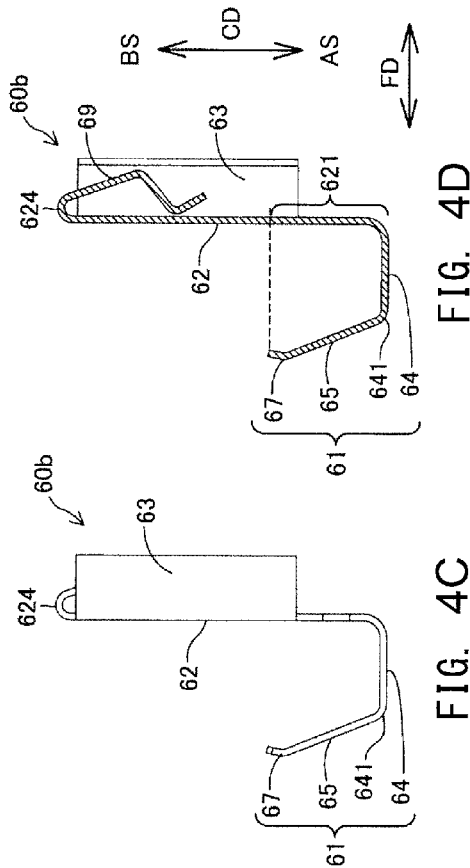
FIG. 4A    FIG. 4B    FIG. 4C    FIG. 4D

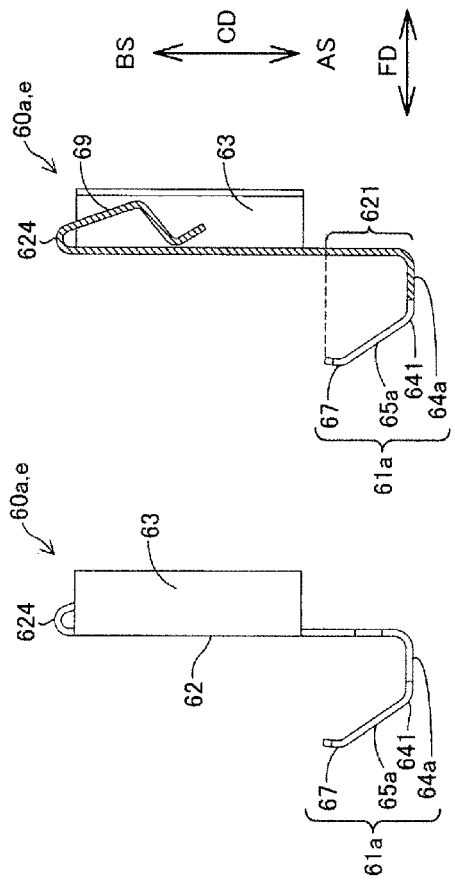

SENSOR

This application claims the benefit of Japanese Patent Application No. 2015-002895, filed Jan. 9, 2015, which is incorporated herein by reference in its entity.

FIELD OF THE INVENTION

The present invention relates to sensor technologies.

BACKGROUND OF THE INVENTION

Conventionally, a sensor, which is mounted to an intake system (e.g., an intake pipe or an intake manifold) or an exhaust system of an internal combustion engine such as a diesel engine or a gasoline engine, has been known and is used for detecting the concentration of a specific gas component (e.g., oxygen or NOx) in a measurement target gas (e.g., Japanese Laid-Open Patent Publication No. 2007-71582). This sensor includes: a plate-shaped detection element extending in an axial direction and having an electrode terminal portion (electrical connection terminal portion) formed on a rear side of the detection element in the axial direction; a metal terminal member (connection terminal) electrically connected to the electrode terminal portion to form a current path; and a separator into which the metal terminal member is inserted (e.g., Japanese Laid-Open Patent Publication No. 2007-71582).

The metal terminal member disclosed in Japanese Laid-Open Patent Publication No. 2007-71582 includes: an elongated frame body portion extending in the axial direction; and an element contact portion that is folded back from a front end portion of the frame body portion to the rear side in the axial direction, and is in contact with the electrode terminal portion. The metal terminal member has an engagement portion for positioning itself with respect to the separator. The engagement portion protrudes from the frame body portion toward a side opposite to the side where the detection element is located, and is engaged with the separator to regulate movement of the frame body portion.

Problems to be Solved by the Invention

In the technique disclosed in Japanese Laid-Open Patent Publication No. 2007-71582, since the engagement portion protrudes from the frame body portion toward the side opposite to the side where the detection element is located, it is necessary to provide a groove portion for engagement with the engagement portion at an inner wall surface of the separator. Such a groove portion causes the separator to have a portion having a small thickness in a radial direction thereof. In this case, it is necessary to increase the dimension of the separator in the radial direction, in order to suppress a reduction in the strength of the separator by eliminating the portion of the separator having the small thickness in the radial direction. This causes a problem of an increase in the size of the sensor in the radial direction.

Further, in the process of manufacturing the sensor, the element contact portion may be pressed by the detection element and move along the axial direction. In addition, the element contact portion may move along the axial direction when an external force is applied to the element contact portion due to, for example, vibration or the like of a portion to which the sensor is mounted. Therefore, in order to reliably achieve contact between the element contact portion and the electrode terminal portion of the detection element, the electrode terminal portion needs to be formed large in size along the axial direction, taking into account the amount of movement of the element contact portion. If the size of the electrode terminal portion is increased, the manufacturing cost of the entire sensor may be increased.

The above-mentioned problem is not limited to a gas sensor but is common to various sensors such as a temperature sensor, a pressure sensor, etc.

SUMMARY OF THE INVENTION

Means for Solving the Problems

The present invention has been made to solve the above problems and can be embodied in the following modes or applications.

(1) According to an aspect of the present invention, a sensor is provided which includes: a detection element having a first main surface, a second main surface opposed to the first main surface, a plate shape extending in an axial direction, and an electrical connection terminal portion that is formed at a rear side of the detection element in the axial direction; a separator including an insertion portion into which the rear side of the detection element is inserted, and a plurality of terminal housing portions that are disposed surrounding a circumference of the insertion portion around the axial direction, and extend in the axial direction; and a connection terminal that is sandwiched and held between the detection element and the separator while being inserted into at least one of the plurality of terminal housing portions, and is electrically connected to the electrical connection terminal portion to form a current path. A front side of the detection element in the axial direction is directed to a measurement target. The connection terminal includes: an elongated frame body portion extending in the axial direction; and an element contact portion that is folded back from a front end portion of the frame body portion and extends to the rear side and in a direction approaching the detection element, and is in contact with the electrical connection terminal portion. The sensor further includes a first regulation portion that is provided at a position closer to the detection element relative to the frame body portion, in an opposing direction in which the first main surface and the second main surface oppose each other, and regulates movement of the frame body portion in the direction approaching the detection element.

According to the sensor of this aspect, since the first regulation portion is provided at a position closer to the detection element relative to the frame body portion, an increase in the size of the separator in the radial direction can be suppressed. Further, since the movement of the frame body portion is regulated by the first regulation portion, the amount of movement of the element contact portion along the axial direction can be reduced. Thereby, the electrical connection terminal portion and the element contact portion can be brought into contact with each other while suppressing an increase in the dimension of the electrical connection terminal portion along the axial direction.

(2) In the sensor of the above aspect, the first regulation portion may regulate the movement of the frame body portion by contacting the frame body portion in a state where the connection terminal is assembled as a component of the sensor.

According to the sensor of this aspect, in the assembled state where the connection terminal is assembled as a component of the sensor, the movement of the frame body portion can be regulated by the first regulation portion being in contact with the frame body portion. Accordingly, positional deviation of the element contact portion along the axial direction in the assembled state can be suppressed. Thus, contact between the element contact portion and the electrical connection terminal portion can be favorably maintained while suppressing an increase in the dimension of the electrical connection terminal portion along the axial direction.

(3) In the sensor of the above aspect, the first regulation portion may be configured to regulate the movement of the frame body portion by contacting the frame body portion in an assembling process where the rear side of the detection element is disposed at the insertion portion while the connection terminal is inserted into the terminal housing portion.

According to the sensor of this aspect, in the assembling process, the movement of the frame body portion can be regulated by the first regulation portion being in contact with the frame body portion. Thereby, the amount of movement of the element contact portion along the axial direction can be reduced in the assembling process. Thus, the element contact portion and the electrical connection terminal portion can be brought into contact with each other while suppressing an increase in the dimension of the electrical connection terminal portion along the axial direction.

(4) In the sensor of the above aspect, the first regulation portion may be provided in the separator.

According to the sensor of this aspect, the movement of the frame body portion can be regulated by the first regulation portion as a component of the separator.

(5) In the sensor of the above aspect, the element contact portion may include: an inward extending portion that is connected to the front end portion of the frame body portion, and extends from the frame body portion to a side where the detection element is located; and a spring portion that is connected to an inward end portion of the inward extending portion, where the detection element is located, and extends in a direction from the inward extending portion to the rear side in the axial direction, the spring portion forming a terminal contact portion to be in contact with the electrical connection terminal portion. The sensor may further include a second regulation portion that is located on the rear side relative to the inward extending portion, and regulates movement of the inward extending portion to the rear side.

According to the sensor of this aspect, since the movement of the inward extending portion to the rear side can be regulated by the second regulation portion, the amount of movement of the terminal contact portion along the axial direction can be further reduced. Thus, the terminal contact portion and the electrical connection terminal portion can be brought into contact with each other while further suppressing an increase in the dimension of the electrical connection terminal portion along the axial direction.

(6) In the sensor of the above aspect, the second regulation portion may regulate the movement of the inward extending portion by contacting the inward extending portion in the state where the connection terminal is assembled as a component of the sensor.

According to the sensor of this aspect, in the assembled state where the connection terminal is assembled as a component of the sensor, the movement of the inward extending portion can be regulated by the second regulation portion being in contact with the inward extending portion. Accordingly, positional deviation of the terminal contact portion along the axial direction in the assembled state can be suppressed. Thus, contact between the terminal contact portion and the electrical connection terminal portion can be favorably maintained while suppressing an increase in the dimension of the electrical connection terminal portion along the axial direction.

(7) In the sensor of the above aspect, the second regulation portion may be configured to regulate the movement of the inward extending portion by contacting the inward extending portion in an assembling process where the rear side of the detection element is disposed at the insertion portion while the connection terminal is inserted into the terminal housing portion.

According to the sensor of this aspect, in the assembling process, the movement of the inward extending portion can be regulated by the second regulation portion being in contact with the inward extending portion. Thereby, in the assembling process, the amount of movement of the terminal contact portion along the axial direction can be reduced. Thus, the terminal contact portion and the electrical connection terminal portion can be brought into contact with each other while suppressing an increase in the dimension of the electrical connection terminal portion along the axial direction.

(8) In the sensor of the above aspect, the first regulation portion and the second regulation portion may be formed of a single common member.

According to the sensor of this aspect, since the first and second regulation portions are formed of a single common member, the number of components can be reduced.

(9) In the sensor of the above aspect, the second regulation portion may be provided in the separator.

According to the sensor of this aspect, the movement of the inward extending portion can be regulated by the second regulation portion as a component of the separator.

The present invention can be embodied in various forms other than the sensor. For example, the present invention can be embodied in forms such as a method for manufacturing a sensor.

BRIEF DESCRIPTION OF THE DRAWINGS

These and other features and advantages of the present invention will become more readily appreciated when considered in connection with the following detailed description and appended drawings, wherein like designations denote like elements in the various views, and wherein:

FIGS. 4(A), 4(B), 4(C) and 4(D) are diagrams for explaining a second connection terminal.

FIGS. 5(A), 5(B), 5(C) and 5(D) are diagrams for explaining third and fourth connection terminals.

DETAILED DESCRIPTION OF THE INVENTION

A. Embodiment

Figure 1:
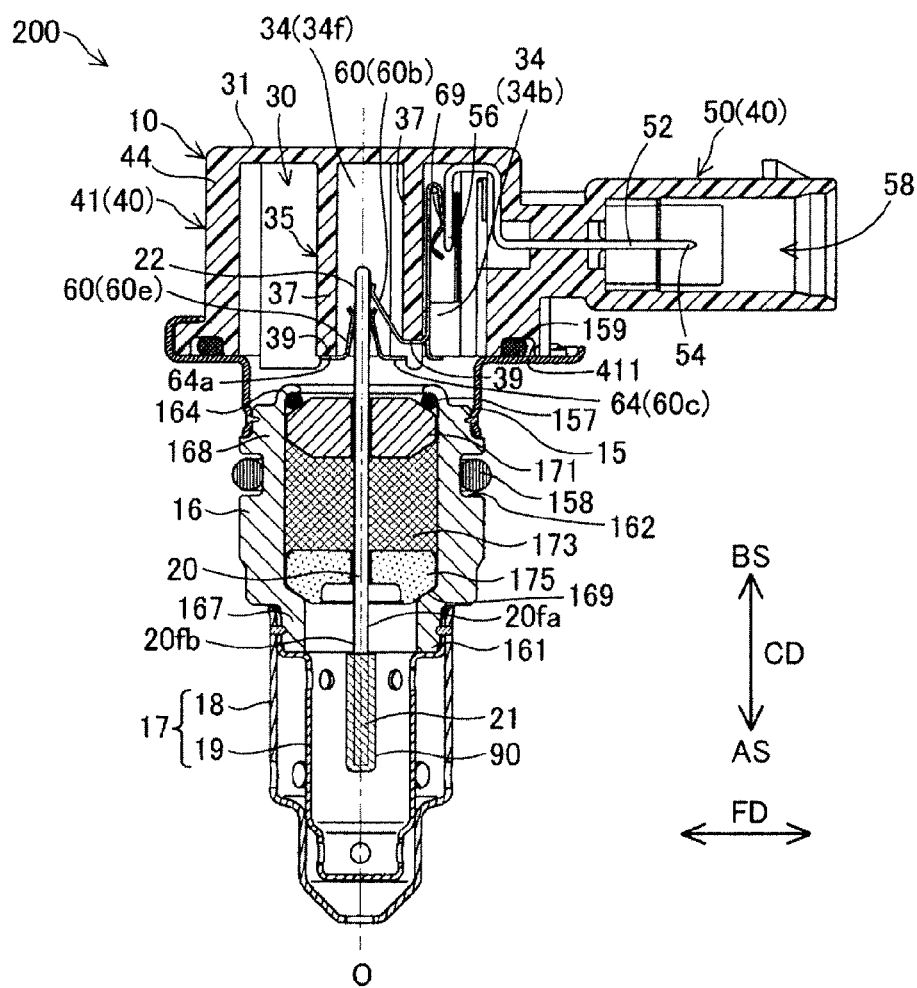
FIG. 1 is a cross-sectional view of a sensor as an embodiment of the present invention.
Figure 2:
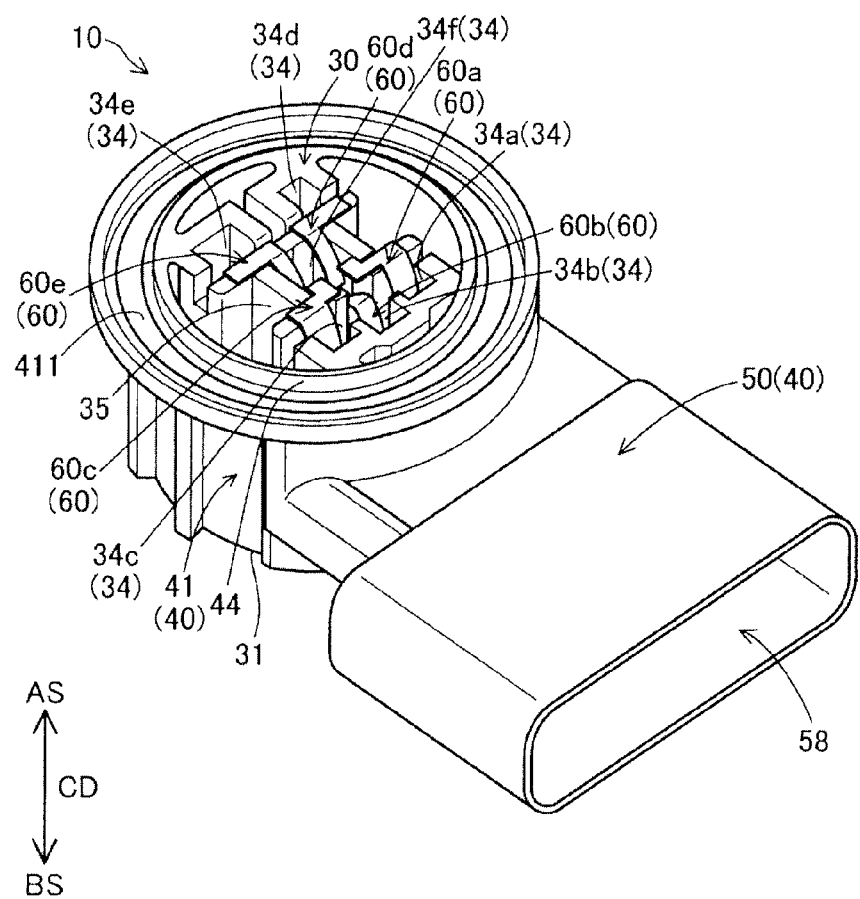
FIG. 2 is a perspective view of a terminal housing unit.
Figure 3:
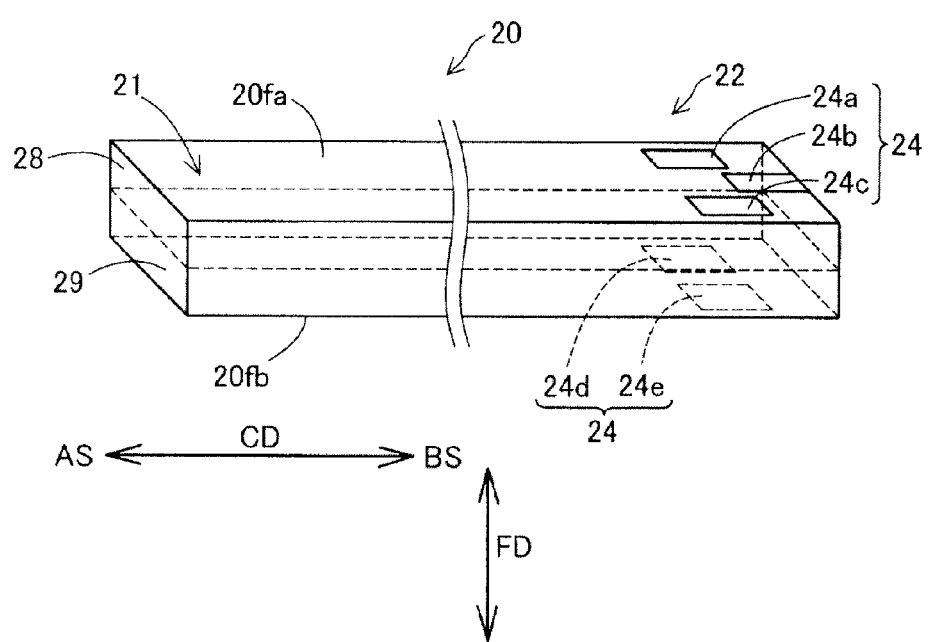
FIG. 3 is a perspective view of a detection element.

FIG. 1 is a cross-sectional view of a sensor 200 as an embodiment of the present invention. FIG. 2 is a perspective view of a terminal housing unit 10. FIG. 3 is a perspective view of a detection element 20. In FIG. 1, a direction parallel to an axis O of the detection element 20 is referred to as an axial direction CD, the upper side in the sheet of FIG. 1 is referred to as a rear side BS of the sensor 200, and the lower side in the sheet of FIG. 1 is referred to as a front side AS of the sensor 200. This sensor 200 is mounted to, for example, an intake system of an internal combustion engine, and outputs a detection signal for detecting the concentration of oxygen in a measurement target gas that flows in the intake system.

The sensor 200 (FIG. 1) includes, in order from the rear side BS to the front side AS, the terminal housing unit 10, an attachment portion 15, a metal shell 16, and a protector 17. The sensor 200 further includes the detection element 20 extending in the axial direction CD.

The detection element 20 has a plate shape, and has a first plate surface 20fa and a second plate surface 20fb which extend in the axial direction CD and oppose each other. The first plate surface 20fa and the second plate surface 20fb each form a main surface of the detection element 20, and each have a largest area among outer surfaces of the detection element 20. A direction in which the first plate surface 20fa and the second plate surface 20fb oppose each other is referred to as an opposing direction FD.

As shown in FIG. 3, the detection element 20 includes: a detection portion 21 located on the front side AS in the axial direction CD; and an element rear end portion 22 located on the rear side BS in the axial direction CD. The element rear end portion 22 includes: first to third metal terminal portions 24a to 24c formed on the first plate surface 20fa; and fourth and fifth metal terminal portions 24d and 24e formed on the second plate surface 20fb. Each of the metal terminal portions 24a to 24e is formed of a metal such as platinum or a member having conductivity, and has a substantially rectangular surface. The second metal terminal portion 24b is disposed on the rear side BS relative to other metal terminal portions 24a, 24c, 24d, and 24e. In the present embodiment, when the first to fifth metal terminal portions 24a to 24e are referred to without being distinguished from each other, they are referred to as "metal terminal portion 24". A metal terminal portion 24 corresponds to an "electrical connection terminal portion" described in the section of Problems to be Solved by the Invention. The detection portion 21 is directed to a gas to be measured which is a measurement target, and is used for detecting the concentration of a specific gas component (e.g., oxygen) in the measurement target gas. As shown in FIG. 1, a front-side portion of the detection element 20, in which the detection portion 21 is located, is covered with a detection portion protection layer 90 formed of a porous member.

The detection element 20 (FIG. 3) is used as an air-fuel ratio sensor, and has the same structure as the conventional detection element. Therefore, the schematic structure thereof is described below while omitting detailed description for the internal structure thereof. The detection element 20 is a stacked body in which a plate-shaped element layer 28 including the detection portion 21 and a plate-shaped heater layer 29 for heating the element layer 28 are stacked. The element layer 28 has a structure in which a solid electrolyte containing zirconia as a principal component and a pair of electrodes containing platinum as a principal component are stacked via an insulating layer having a portion in which a hollow measurement chamber is formed. The element layer 28 includes an oxygen pump cell in which one (also referred to as "first electrode") of the pair of electrodes formed on the both surfaces of the solid electrolyte is exposed to the outside while the other one (also referred to as "second electrode") of the pair of electrodes is disposed in the measurement chamber. Further, the element layer 28 includes an oxygen concentration measurement cell in which the second electrode is disposed in a reference gas chamber. The element layer 28 is configured to control a current that flows across the pair of electrodes of the oxygen pump cell so that an output voltage of the oxygen concentration measurement cell has a predetermined value, thereby to pump out oxygen from the measurement chamber, or pump oxygen from the outside into the measurement chamber. In the oxygen pump cell, the pair of electrodes and a portion of the solid electrolyte sandwiched between these electrodes constitute the detection portion 21 in which a current according to the oxygen concentration flows. The metal terminal portions 24 are used to take a detection signal from the detection portion 21, and supply a power to a heating wire embedded in the heater layer 29.

The terminal housing unit 10 (FIG. 1) includes: a bottomed-tubular-shaped separator portion 30 having a bottom portion 31 on the rear side BS; and a bottomed-tubular-shaped base portion 40 having the bottom portion 31 as its own bottom portion. That is, the separator portion 30 and the base portion 40 share the bottom portion. The base portion 40 has a tubular main body portion 41 surrounding the circumference of the separator portion 30, and a connector portion 50 extending from the main body portion 41 in a direction intersecting the axial direction CD. In the present embodiment, the connector portion 50 extends in a direction orthogonal to the axial direction CD. The terminal housing unit 10 is integrally molded using a resin member. Examples of the resin member may include resins having excellent moldability, such as nylon (trademark), PA (polyamide), PBT (polybutylene-terephthalate), PPS (polyphenylene sulfide), etc.

The separator portion 30 (FIG. 2) includes: first to sixth housing space portions 34a to 34f for housing the detection element 20 and later-described first to fifth connection terminals 60a to 60e; and a partition 35 separating the six housing space portions 34a to 34f from each other. As shown in FIG. 1, the partition 35 is composed of a plurality of plate-shaped members extending from the bottom portion 31 to the vicinity of a front-side end surface of the separator portion 30. At a plane orthogonal to the axial direction CD, the partition 35 separates the first to sixth housing space portions 34a to 34f from each other. The partition 35 regulates movements of the first to fifth connection terminals 60a to 60e. A method of regulating the movements of the first to fifth connection terminals 60a to 60e will be described later. The first to sixth housing space portions 34a to 34f extend in the axial direction CD. The first to fifth housing space portions 34a to 34e are disposed surrounding the circumference of the sixth housing space portion 34f around the axial direction CD.

In the first to fifth housing space portions 34a to 34e, the corresponding first to fifth connection terminals 60a to 60e (specifically, later-described frame body portions of the first to fifth connection terminals 60a to 60e) are inserted, respectively. In the sixth housing space portion 34f, the element rear end portion 22 of the detection element 20 and part of the first to fifth connection terminals 60a to 60e (specifically, part of later-described element contact portions of the first to fifth connection terminals 60a to 60e) are inserted. The first to fifth connection terminals 60a to 60e are electrically connected to each other by contacting the corresponding first to fifth metal terminal portions 24a to 24e. Thus, the first to fifth connection terminals 60a to 60e form a current path between the detection element 20 and an external device for calculating the concentration of oxygen. When the first to fifth connection terminals 60a to 60e are referred to without being distinguished from each other, they are referred to as "connection terminals 60". As shown in FIG. 1, the first to fifth connection terminals 60a to 60e (in FIG. 1, refer to the second connection terminal 60b) are inserted into the corresponding first to fifth housing space portions 34a to 34e. In addition, the connection terminals 60 are sandwiched and held between the detection element 20 and the separator portion 30. That is, each connection terminal 60 is sandwiched and held between the detection element 20 and the separator portion 30 while being inserted into one of the plurality of housing space portions 34a to 34e.

As shown in FIG. 2, when the separator portion 30 is viewed from the front side AS, the sixth housing space portion 34f is disposed substantially in the center of the tubular separator portion 30, and the first to fifth housing space portions 34a to 34e are disposed outward in the radial direction of the separator portion 30 relative to the sixth housing space portion 34f. When the first to sixth housing space portions 34a to 34f are referred to without being distinguished from each other, they are referred to as "housing space portions 34". The structure of the separator portion 30 will be described later in detail. The first to fifth housing space portions 34a to 34e correspond to "terminal housing portions" described in the section of Problems to be Solved by the Invention, and the sixth housing space portion 34f corresponds to "insertion portion" described in the section of Problems to be Solved by the Invention.

The main body portion 41 of the base portion 40 has a side portion 44 surrounding the circumference of the separator portion 30. The side portion 44 extends from a circumferential edge of the bottom portion 31 located on the rear side BS in the axial direction CD to the front side AS in the axial direction CD. The side portion 44 is disposed surrounding the circumference of the separator portion 30 in the radial direction. As shown in FIG. 1, the partition 35 and the side portion 44 are indirectly connected via the bottom portion 31. Further, as shown in FIG. 2, the partition 35 and the side portion 44 are connected to each other on at least the front side AS. On a front-side end surface of the main body portion 41, a groove 411 is formed over the circumferential direction. The structure of the main body portion 41 will be described later in detail.

In the connector portion 50 (FIG. 1), connector terminals 52 (specifically, one end portions of the connector terminals 52) for taking a detection signal outputted from the detection element 20 to the outside are housed. Five connector terminals 52 are provided corresponding to the number of the connection terminals 60 (only one of them is shown in FIG. 1). The connector terminals 52 are mounted to the base portion 40 by being molded to be inserted into the base portion 40. That is, resin of the base portion 40 and the connector terminals 52 are resin-molded. More specifically, the connector terminals 52 are placed in a die, and a resin is injected around the connector terminals 52, whereby the connector terminals 52 are mounted to the base portion 40. The insert molding allows the connector terminals 52 to be easily fixed to the base portion 40.

The other end portions 56 of the respective connector terminals 52 are electrically connected to the corresponding connection terminals 60 in the first to fifth housing space portions 34a to 34e. The one end portions 54 of the connector terminals 52 are disposed in an opening portion 58 of the connector portion 50, and external connectors are inserted into the opening portion 58, whereby the external connectors are connected to the one end portions 54 of the connector terminals 52. Thus, a detection signal is transmitted via the external connectors to a measurement device for calculating the concentration of oxygen.

The metal shell 16 is a tubular member in which the detection element 20 is disposed. The metal shell 16 is formed of stainless steel such as SUS430. The metal shell 16 surrounds the circumference of the detection element 20 around the axial direction CD. The metal shell 16 holds the detection element 20 such that the detection portion 21 of the detection element 20 protrudes to the front side AS, and the element rear end portion 22 thereof protrudes to the rear side BS. The attachment portion 15 is mounted to a rear-side circumferential portion 168 of the metal shell 16, located on the rear side BS, by laser beam welding or the like. The protector 17 is mounted to a front-side circumferential portion 167 of the metal shell 16, located on the front side AS, by laser beam welding.

The metal shell 16 further includes a groove portion 162 formed over the entire circumference of the metal shell 16, at a position between the rear-side circumferential portion 168 and the front-side circumferential portion 167 in the axial direction CD. In the groove portion 162, a seal member 158 is disposed. In the present embodiment, the seal member 158 is an O-ring. The seal member 158 seals a space between the sensor 200 and a mounting target. Specifically, when the sensor 200 is mounted to the mounting target, the seal member 80 is deformed by being pressure-welded to an inner wall of a sensor mounting hole, and seals a space between the sensor mounting hole and the sensor 200.

In the metal shell 16, a tubular ceramic holder 175 made of alumina, a powder-charged layer 173 made of talc powder, and a tubular ceramic sleeve 171 made of alumina are disposed in order from the front side AS to the rear side BS. Further, a crimp ring 157 is disposed between the ceramic sleeve 171 and a rear end portion 164 of the metal shell 16.

The ceramic holder 175 is engaged with a ledge portion 169 of the metal shell 16, located on the front side AS. The ceramic sleeve 171 is a tubular member having a rectangular axial bore along the axial direction CD. The ceramic sleeve 171 and the ceramic holder 175 support the detection element 20 in such a manner that the plate-shaped detection element 20 is inserted into the rectangular axial bore along the axial direction CD. After the ceramic sleeve 171 is mounted to the metal shell 16, the ceramic sleeve 171 is fixed in the metal shell 16 by bending the rear end portion 164 of the metal shell 16 inward in the radius direction, and crimping the rear end portion 164 via the crimp ring 157 toward a rear end surface of the ceramic sleeve 171.

The protector 17 (FIG. 1) has an external protector 18, and an internal protector 19 located inside the external protector 18. The external protector 18 and the internal protector 19 each have a bottomed tubular shape. The external protector 18 and the internal protector 19 are members made of a metal and having a plurality of holes. A measurement target gas flows into the internal protector 19 through the plurality of holes. The external protector 18 and the internal protector 19 cover the detection portion 21 of the detection element 20 to protect the detection portion 21 from water or the like from the outside.

The attachment portion 15 is a member connecting the metal shell 16 and the terminal housing unit 10. The attachment portion 15 is a member made of a metal such as stainless steel. A part of the attachment portion 15, located on the front side AS, is mounted to the metal shell 16 by laser beam welding or the like, and a part of the attachment portion 15, located on the rear side BS, is mounted to the base portion 40 of the terminal housing unit 10 by crimping. A seal member 159 is disposed in the groove 411 formed on a front-side end surface of the base portion 40 (specifically, the main body portion 41). The seal member 159 is an O-ring. This seal member 159 seals an attachment portion between the attachment portion 15 and the base portion 40. The attachment portion 15 has a pair of flange portions (not shown) protruding in a direction perpendicular to the sheet of FIG. 1. Holes are formed in the flange portions. The sensor 200 is mounted to the mounting target by inserting screws into the holes and fixing the screws in screw holes formed in the mounting target.

FIGS. 4(A)-4(D) are diagrams for explaining the second connection terminal 60b. FIG. 4(A) is a top view of the second connection terminal 60b. FIG. 4(B) is a front view of the second connection terminal 60b. FIG. 4(C) is a right side view of the second connection terminal 60b. FIG. 4(D) is a cross-sectional view taken along F4a-F4a in FIG. 4(A). In FIG. 4(D), the axial direction CD and the opposing direction FD in the case where the second connection terminal 60b is assembled in the sensor 200 are shown. FIGS. 4(A)-4(D) show the second connection terminal 60b in the free state, which is not in contact with the detection element 20.

As shown in FIG. 4(D), the second connection terminal 60b has a connector contact portion 69, a frame body portion 62, an element contact portion 61, a projecting portion 63, and two engagement portions 68 (FIG. 4(D)). As shown in FIG. 4(D), the frame body portion 62 has an elongated plate shape, and extends in the axial direction CD.

The element contact portion 61 is folded back from a front end portion 621 of the frame body portion 62 and extends to the rear side BS. The element contact portion 61 has: an inward extending portion 64 extending from the front end portion 621 of the frame body portion 62 toward the side where the detection element 20 is located (extending in the direction approaching the detection element 20) along the opposing direction FD; and a spring portion 65 that is connected to an inward end portion 641 of the inward extending portion 64, which is an end portion on the side where the detection element 20 is located, and extends in a direction from the inward extending portion 64 to the rear side BS in the axial direction CD. The inward extending portion 64 of the present embodiment extends linearly along the horizontal direction. The spring portion 65 extends so as to approach the detection element 20 toward the rear side BS. A portion of the spring portion 65, located on the rear side BS, is in contact with the metal terminal portion 24, whereby a terminal contact portion 67 electrically in contact with the metal terminal portion 24 is formed. The front end portion 621 of the frame body portion 62 is a portion of the frame body portion 62, corresponding to a range where the element contact portion 61 is located in the axial direction CD.

The connector contact portion 69 is folded back from a rear end portion 624 of the frame body portion 62 and extends to the front side AS. The connector contact portion 69 is folded back to the side opposite to the side where the element contact portion 61 is located, with respect to the frame body portion 62. As shown in FIG. 4(A) and FIG. 4(D), the projecting portion 63 extends from the frame body portion 62 to the side opposite to the side where the element contact portion 61 is located. The projecting portion 63 is formed so as to enclose the connector contact portion 69. The projecting portion 63 is housed in the second housing space portion 34b and is in contact with a wall surface of the second housing space portion 34b, whereby movement of the second connection terminal 60b is regulated. As shown in FIG. 4(B), the two engagement portions 68 are plate-shaped members protruding from the frame body portion 62 on the front side AS to the width direction of the frame body portion 62. The two engagement portions 68 are disposed in the groove formed at the front-side end surface of the separator portion 30, and are engaged with the separator portion 30, whereby deformation of the frame body portion 62 toward the detection element 20 side is suppressed.

FIGS. 5(A)-5(D) are diagrams for explaining the first and fifth connection terminals 60a, 60e. FIG. 5(A) is a top view of the first (fifth) connection terminal 60a (60e). FIG. 5(B) is a front view of the first (fifth) connection terminal 60a (60e). FIG. 5(C) is a right side view of the first (fifth) connection terminal 60a (60e). FIG. 5(D) is a cross-sectional view taken along F5a-F5a in FIG. 5(A). In FIG. 5(D), the axial direction CD and the opposing direction FD in the case where the first (fifth) connection terminal 60a (6e) is assembled in the sensor 200 are shown. The first and fifth connection terminals 60a, 60e are different from the second connection terminal 60b (FIGS. 4(A)-4(D)) in the number of the engagement portions 68 and the structure of the element contact portion 61a. Since other components of the first and fifth connection terminals 60a, 60e are identical to those of the second connection terminal 60b, the same components are designated by the same reference numerals, and the description thereof is omitted. FIGS. 5(A)-5(D) show the first (fifth) connection terminal 60a (60e) in the free state, which is not in contact with the detection element 20.

Only one engagement portion 68 (FIG. 5(B)) is provided. The engagement portion 68 protrudes from the frame body portion 62 on the front side AS in the width direction of the frame body portion 62. As shown in FIG. 5(C), the element contact portion 61a is folded back from the front end portion 621 of the frame body portion 62 and extends to the rear side BS. The element contact portion 61a is different from the element contact portion 61 (FIGS. 4(A)-4(D)) of the second connection terminal 60b in that an inward extending portion 64a has a bent portion in the width direction of the frame body portion 62, and that the width of a spring portion 65a is smaller than the width of the spring portion 65 (FIGS. 4(A)-4(D)). As shown in FIG. 5(A) and FIG. 5(B), the inward extending portion 64a extends linearly along the horizontal direction, and a portion thereof on the side where the spring portion 65a is connected is bent in the width direction of the frame body portion 62. The bending direction is opposite to the direction in which the engagement portion 68 protrudes.

The third and fourth connection terminals 60c, 60d (FIG. 2) are different from the first and fifth connection terminals 60a, 60e only in that the positions of the engagement portion 68 and the element contact portion 61a with respect to the frame body portion 62 are opposite to those of the first and fifth connection terminals 60a, 60e. That is, in the case of the third and fourth connection terminals 60c, 60d, in FIG. 5(B), the engagement portion 68 is located on the left side with respect to the frame body portion 62, and the spring portion 65a is located on the right side with respect to the frame body portion 62.

Figure 6:
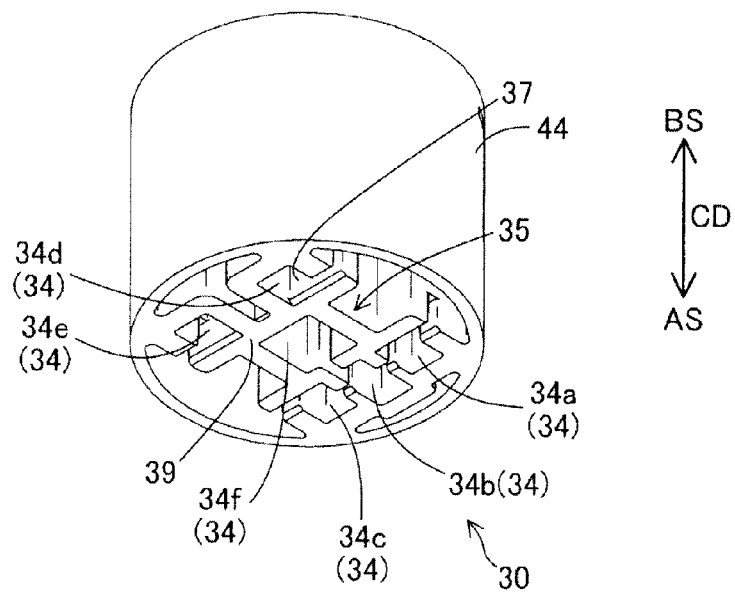
FIG. 6 is a perspective view showing a separator portion and a side portion of a base portion.
Figure 7:
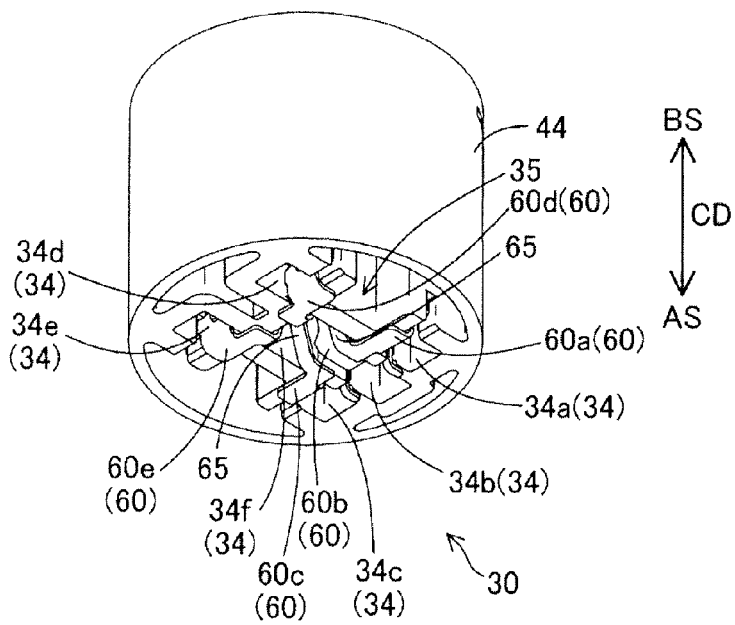
FIG. 7 is a perspective view showing the separator portion in which a connection terminal is disposed.
Figure 8:
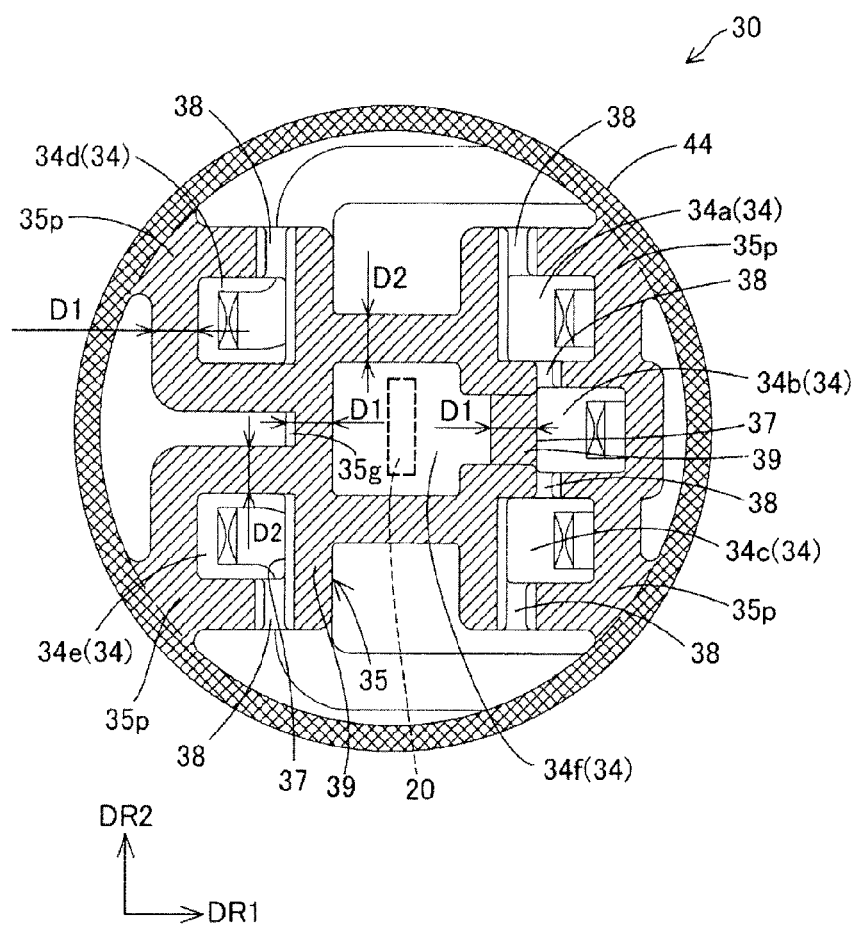
FIG. 8 is a view of the structure shown in FIG. 6 as viewed from the front side.
Figure 9:
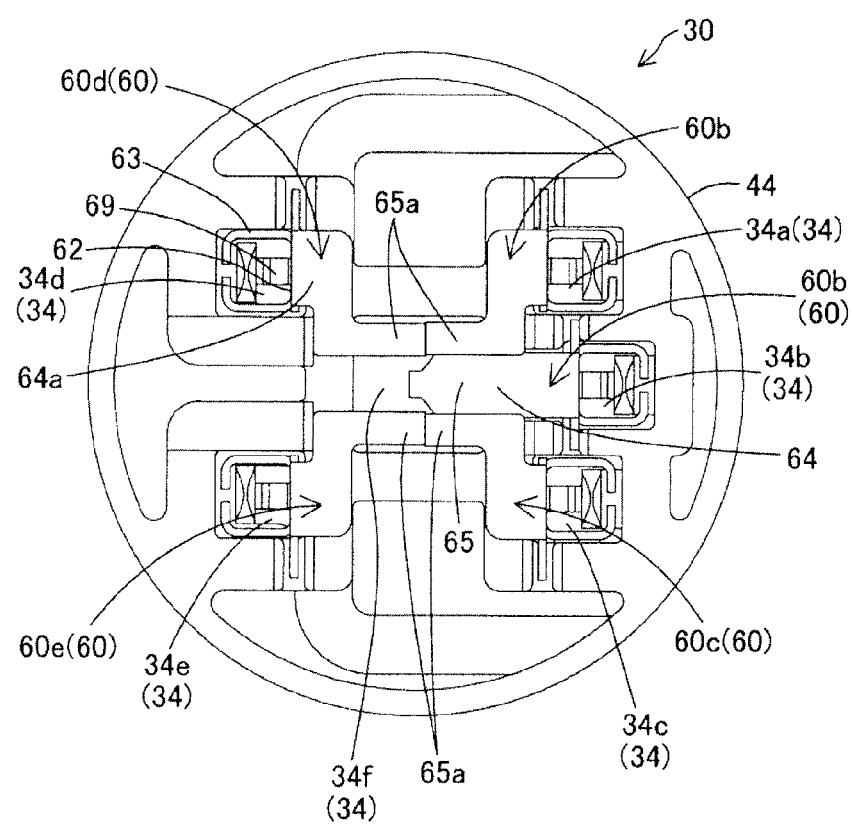
FIG. 9 is a view of the structure shown in FIG. 7 as viewed from the front side.

FIG. 6 is a perspective view showing the separator portion 30 and the side portion 44 of the base portion 40. FIG. 7 is a perspective view showing the separator portion 30 in which the connection terminal 60 is disposed. FIG. 8 is a view of the structure shown in FIG. 6 as viewed from the front side AS. FIG. 9 is a view of the structure shown in FIG. 7 as viewed from the front side AS. FIG. 6 and FIG. 7 each show a part of the side portion 44 (FIG. 2) inward in the radial direction relative to the groove 411. In FIG. 8, for easy understanding, at the front-side end surface, the side portion 44 is shown with cross-hatching and the partition 35 is shown with single-hatching, and a portion where the detection element 20 is to be disposed is enclosed by a dotted line.

As shown in FIG. 6 and FIG. 7, the partition 35 of the separator portion 30 separates the plurality of housing space portions 34 from each other. Specifically, the plurality of housing space portions 34 are separated from each other by the partition 35 so that each housing space portion 34 has a substantially rectangular cross section orthogonal to the axial direction CD. That is, the partition 35 forms side walls of the housing space portions 34 along the axial direction CD. Thereby, when the connection terminals 60 and the detection element 20 are disposed in the separator portion 30, the circumference of each of the frame body portions 62 of the connection terminals 60 and the circumference of the detection element 20, around the axial direction CD, are surrounded by the partition 35. As shown in FIG. 8, the front-side end surface of the partition 35 is directly connected to the side portion 44. Specifically, four corner portions 35p of the front-side end surface of the partition 35, which are located outward in the radial direction of the separator portion 30, are connected to the side portion 44. In addition, the partition 35 is indirectly connected to the bottom portion 31 (FIG. 1) of the base portion 40. At the front-side end surface of the partition 35, grooves 38 in which the engagement portions 68 (FIG. 4(A), FIG. 5(B)) of the connection terminals 60 are to be disposed are formed.

As shown in FIG. 1 and FIG. 6, the partition 35 has a first regulation portion 37 extending along the axial direction CD, and a second regulation portion 39. The first regulation portion 37 is a wall portion located between the element rear end portion 22 and the frame body portion 62 with respect to the opposing direction FD. The first regulation portion 37 is located closer to the detection element 20 relative to the frame body portion 62 with respect to the opposing direction FD. Further, the first regulation portion 37 faces the frame body portion 62 in the opposing direction FD. The first regulation portion 37 is a member for regulating the movement of the frame body portion 62 in the direction approaching the detection element 20 with respect to the opposing direction FD.

The second regulation portion 39 is a portion forming a front-side end portion of the partition 35 in the axial direction CD. The second regulation portion 39 is located on the rear side BS relative to the inward extending portion 64, 64a. The second regulation portion 39 faces the inward extending portion 64, 64a in the axial direction CD. The second regulation portion 39 is a member for regulating the movement of the inward extending portion 64, 64a to the rear side BS with respect to the axial direction CD. The first and second regulation portions 37, 39 are portions of the separator portion 30 integrally molded using a resin member. In other words, the first and second regulation portions 37, 39 are formed of a single common member (separator portion 30). Thereby, the number of components of the sensor 200 can be reduced as compared to the case where the first and second regulation portions 37, 39 are provided separately from the separator portion 30.

As shown in FIG. 9, in the first to fifth housing space portions 34a to 34e, the frame body portions 62, the projecting portions 63, and the connector contact portions 69 of the corresponding connection terminals 60 are housed. In the sixth housing space portion 34f, the element rear end portion 22 (FIG. 1) of the detection element 20 and the spring portion 65, 65a of the connection terminal 60 are housed. As shown in FIG. 8, at the cross section orthogonal to the axial direction CD, thicknesses D1 and D2 of the partition 35 are preferably fixed. Thereby, when the separator portion 30 is formed by injection molding or the like using a resin member, it is possible to suppress unevenness in the degree of thermal contraction at each portion of the separator portion 30. Thus, the separator portion 30 can be formed with high accuracy. The front-side end surface of the partition 35 is partially chamfered to form chamfered portions 35g. In another embodiment, the thickness of the partition 35 may not be fixed.

The thicknesses D1 and D2 of the partition 35 are thicknesses in the following first and second directions orthogonal to the axial direction CD.

First direction DR1: a direction orthogonal to the axial direction CD, in which the first plate surface 20fa and the second plate surface 20fb of the detection element 20 oppose each other.

Second direction DR2: a direction orthogonal to the axial direction CD and to the first direction DR1.

In the present embodiment, the thickness of the partition 35 in the first direction DR1 is the thickness D1, and the thickness of the partition 35 in the second direction DR2 is the thickness D2.

Figure 10:
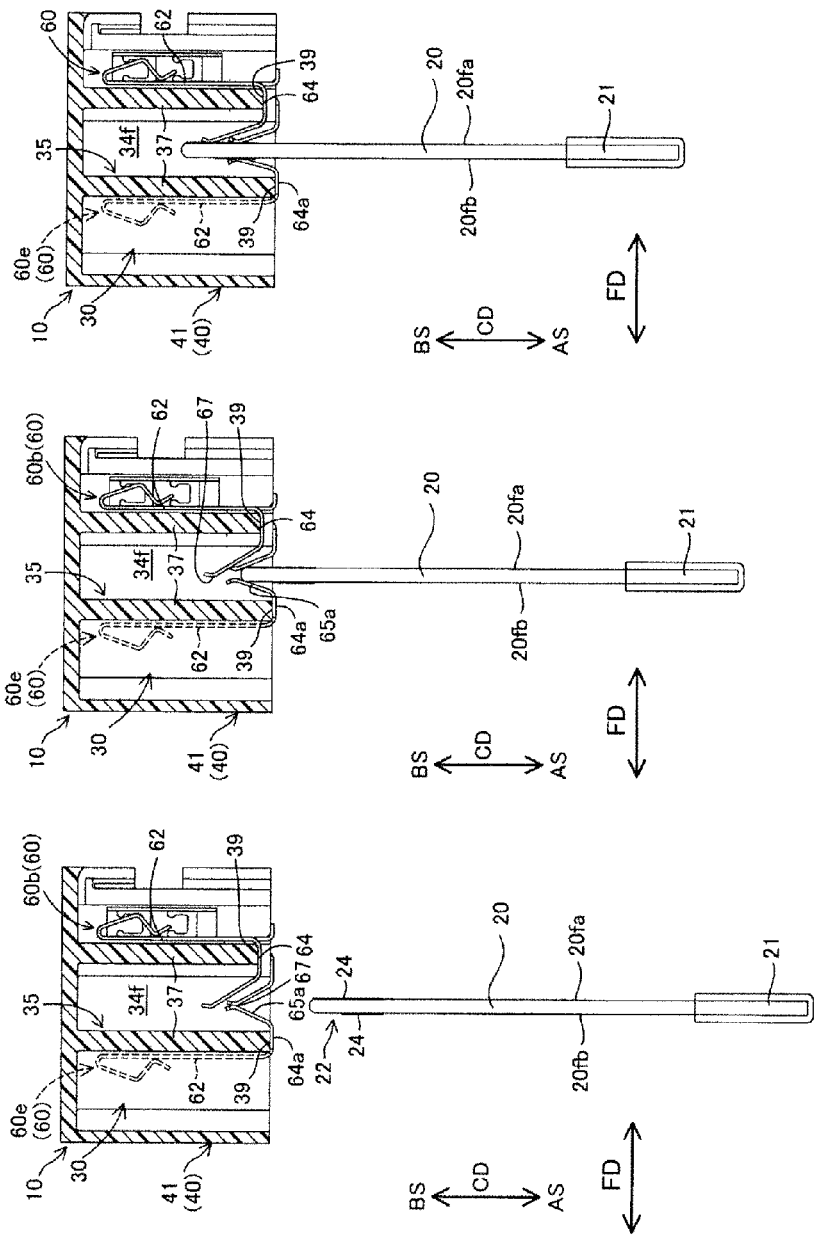
FIGS. 10(A), 10(B) and 10(C) are diagrams for explaining a part of a sensor manufacturing process.

FIGS. 10(A)-10(C) are diagrams for explaining a part of a process of manufacturing the sensor 200. Specifically, FIGS. 10(A)-10(C) show an assembling process of setting the element rear end portion 22 of the detection element 20 in the sixth housing space portion 34f as an insertion portion. In order from FIG. 10( ) to FIG. 10(C), the detection element 20 is moved from the front side AS to the rear side BS along the axial direction CD. In the state shown in FIG. 10(B), the detection element 20 comes into contact with the spring portion 65a and elastically deforms the spring portion 65a. In the state shown in FIG. 10(C), contact between the metal terminal portions 24 and the terminal contact portions 67 is completed.

The manufacturing process of the sensor 200 (FIG. 1) includes a step of disposing the connection terminals 60 in the terminal housing unit 10 and disposing the seal member 159 in the groove 411 and then mounting the attachment portion 15 to the terminal housing unit 10 to prepare a unit member. In addition, the manufacturing process includes a step of disposing the ceramic holder 175, the powder-charged layer 173, and the ceramic sleeve 171 in the metal shell 16, and causing the detection element 20 to be held in the metal shell 16 to prepare an element unit member. Then, the element rear end portion 22 of the detection element 20 is disposed in the sixth housing space portion 34f such that the metal terminal portions 24 of the detection element 20 included in the element unit member come into contact with the terminal contact portions 67 of the connection terminals 60 included in the unit member (assembling process; FIGS. 10(A) to 10(C)). Then, as shown in FIG. 1, the attachment portion 15 and the rear-side circumferential portion 168 are mounted to each other by welding or the like (unit mounting process). The protector 17 and the seal member 158 may be assembled as parts of the element unit when the element unit is prepared, or may be assembled as parts of the sensor 200 after the unit mounting process.

In the assembling process, the first regulation portion 37 is in contact with the frame body portion 62 during at least a period of time from when contact of the detection element 20 to the spring portion 65, 65a is started as shown in FIG. 10(B) to when contact of the metal terminal portions 24 to the terminal contact portions 67 is completed (FIG. 10(C)). In addition, during this period, the second regulation portion 39 is in contact with the inward extending portion 64, 64a. In the present embodiment, the first regulation portion 37 is in contact with the frame body portion 62 and the second regulation portion 39 is in contact with the inward extending portion 64, 64a during a period of time from when the connection terminals 60 are inserted and disposed in the terminal housing portions 34a to 34e (FIG. 10(A)) to when contact of the metal terminal portions 24 to the terminal contact portions 67 is completed (FIG. 10(C)). Further, in the present embodiment, in the state where the connection terminals 60 are assembled as components of the sensor 200 (the state shown in FIG. 1), the first regulation portion 37 faces the frame body portion 62 in the opposing direction FD, and the second regulation portion 39 faces the inward extending portion 64, 64a in the axial direction CD. In the present embodiment, in the assembled state, the first regulation portion 37 is in contact with the frame body portion 62, and the second regulation portion 39 is in contact with the inward extending portion 64, 64a.

As shown in FIGS. 10(A)-10(C), in the assembling process, the detection element 20 comes into contact with the spring portion 65, 65a to apply an external force to the spring portion 65, 65a. This external force causes the frame body portion 62 to move in the direction approaching the detection element 20, and causes the inward extending portion 64a to move to the rear side BS. However, in the assembling process, the first regulation portion 37 is in contact with the frame body portion 62 to regulate the movement of the frame body portion 62 in the direction approaching the detection element 20. In addition, in the assembling process, the second regulation portion 39 is in contact with the inward extending portion 64, 64a to regulate the movement of the inward extending portion 64, 64a to the rear side BS in the axial direction CD. Thereby, the amount of movement of the element contact portion 61 (specifically, the terminal contact portion 67) along the axial direction CD can be reduced in the assembling process. The reason is described below in detail.

Figure 11:
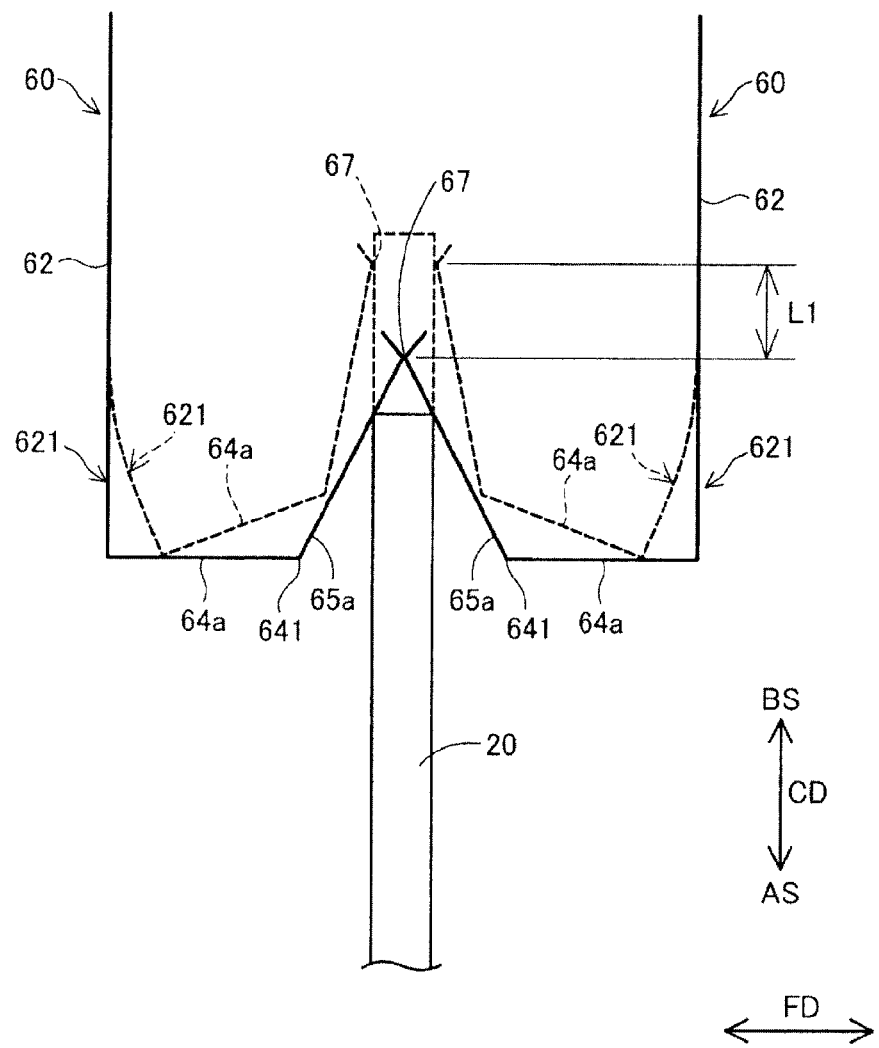
FIG. 11 is a diagram for explaining an amount of movement of a terminal contact portion in a case where first and second regulating portions are not provided.

FIG. 11 is a diagram for explaining the amount of movement of the terminal contact portion 67 in the case where the first and second regulation portions 37, 39 are not provided. In FIG. 11, the explanation is made using the connection terminal 60 (any of the first, third, fourth and fifth connection terminals 60a, 60c, 60d and 60e) having the bent inward extending portion 64a and the spring portion 65a having a small width which are shown in FIGS. 5(A)-5(D). However, the same applies to the connection terminal (second connection terminal 60b) shown in FIGS. 4(A)-4(D). As shown in FIG. 11, when the detection element 20 is moved to the rear side BS along the axial direction CD in the assembling process, the detection element 20 comes into contact with the spring portion 65a. Thereby, the connection terminal 60 is deformed such that the front end portion 621 of the frame body portion 62 moves in the direction approaching the detection element 20 and the inward extending portion 64a moves to the rear side BS in the axial direction CD as shown by dotted lines. In addition, the spring portion 65a is pressed by the detection element 20 and elastically deformed with the inward end portion 641 as a fulcrum. During a period from the free state of the connection terminal 60 to the assembled state after the detection element 20 has been assembled, the above-mentioned deformations cause the terminal contact portion 67 to move to the rear side BS along the axial direction CD by a movement amount L1.

Figure 12:
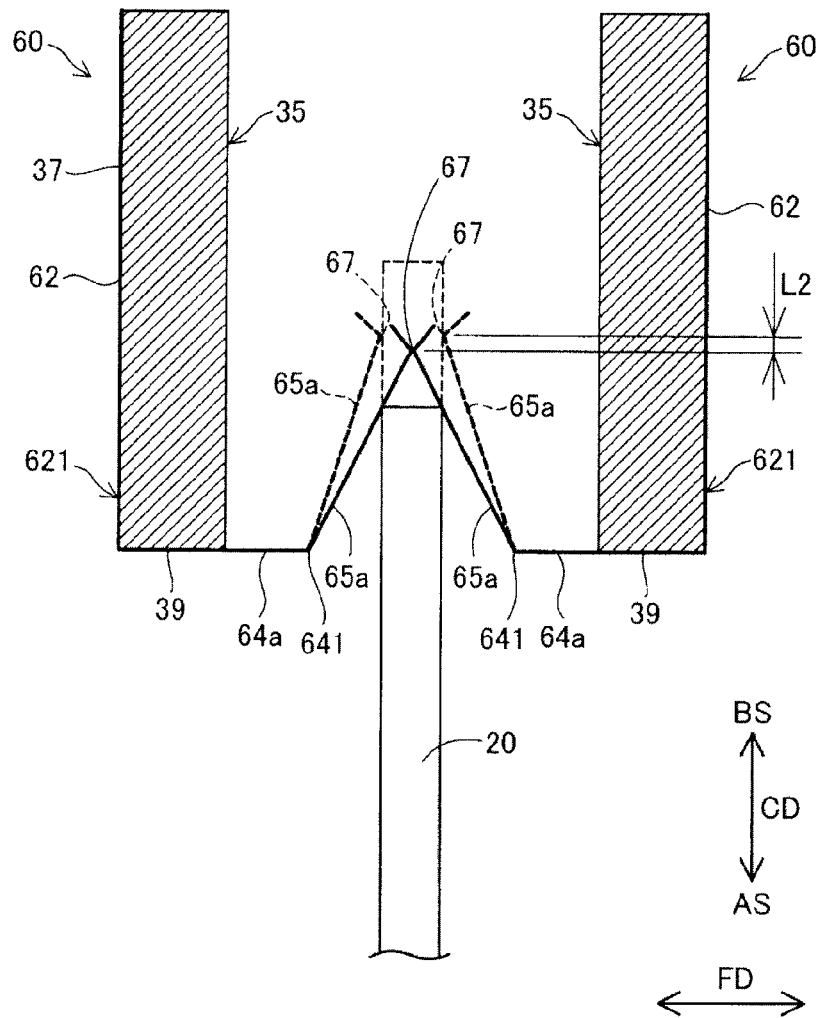
FIG. 12 is a diagram for explaining an amount of movement of a terminal contact portion according to the present embodiment.

FIG. 12 is a diagram for explaining the movement amount of the terminal contact portion 67 according to the present embodiment. In FIG. 12, the explanation is made using the connection terminal 60 (any of the first, third, fourth and fifth connection terminals 60a, 60c, 60d and 60e) having the bent inward extending portion 64a and the spring portion 65a having a small width which are shown in FIGS. 5(A)-5(D). However, the same applies to the connection terminal (second connection terminal 60b) shown in FIGS. 4(A)-4(D). As shown in FIG. 12, movements of the frame body portion 62 and the inward extending portion 64a are regulated by the first and second regulation portions 37, 39 in the assembling process. Thereby, a movement amount L2 from the free state to the assembled state is mainly caused by the elastic deformation of the spring portion 65a, and is smaller than the movement amount L1. Thus, in the present embodiment, the movement amount L2 can be reduced, whereby variation in the contact position, in the axial direction CD, where the terminal contact portion 67 is in contact with the metal terminal portion 24 can be reduced. Accordingly, the terminal contact portion 67 and the metal terminal portion 24 can be brought into contact with each other while suppressing an increase in the dimension of the metal terminal portion 24 along the axial direction. The reduction in the dimension of the metal terminal portion 24 along the axial direction CD leads to a reduction in the manufacturing cost of the sensor 200. Moreover, a reduction in contact failure between the terminal contact portion 67 and the metal terminal portion 24 and a reduction in the area of the terminal contact portion 67 can be achieved.

Further, in the above-mentioned embodiment, since the first regulation portion 37 is located closer to the detection element 20 relative to the frame body portion 62 as shown in FIG. 1, it is not necessary to provide the separator portion 30 with a groove portion or the like for housing the first regulation portion 37. Thus, an increase in the separator portion 30 in the radial direction can be suppressed.

Further, in the above-mentioned embodiment, in the state where the connection terminals 60 are assembled as components of the sensor 200, the first regulation portion 37 faces the frame body portion 62 in the opposing direction FD (FIG. 10(C)). Thus, even when an external force such as an impact is applied to the sensor 200 and thereby the frame body portion 62 attempts to move in the direction approaching the detection element 20, the frame body portion 62 comes into contact with the first regulation portion 37. Thus, the movement of the frame body portion 62 in the direction approaching the detection element 20 can be regulated, whereby positional deviation of the element contact portion 61, 61a (specifically, the terminal contact portion 67) along the axial direction CD in the assembled state can be suppressed. By suppressing the positional deviation, contact between the element contact portion 61, 61a and the metal terminal portion 24 can be favorably maintained while suppressing an increase in the dimension of the metal terminal portion 24 along the axial direction CD.

Furthermore, in the above-mentioned embodiment, in the state where the connection terminals 60 are assembled as components of the sensor 200, the second regulation portion 39 faces the inward extending portion 64, 64a in the axial direction CD (FIG. 10(C)). Thus, even when an external force such as an impact is applied to the sensor 200 and thereby the inward extending portion 64, 64a attempts to move to the rear side BS in the axial direction CD, the inward extending portion 64, 64a comes into contact with the second regulation portion 39. Thus, the movement of the inward extending portion 64, 64a to the rear side BS can be regulated, whereby positional deviation of the element contact portion 61, 61a (specifically, the terminal contact portion 67) along the axial direction CD in the assembled state can be suppressed. By suppressing the positional deviation, contact between the element contact portion 61, 61a and the metal terminal portion 24 can be favorably maintained while suppressing an increase in the dimension of the metal terminal portion 24 along the axial direction CD.

Further, according to the above-mentioned embodiment, the first and second regulation portions 37, 39 are provided in the separator portion 30. Thus, movements of the frame body portion 62 and the inward extending portion 64, 64a can be regulated by the first and second regulation portions 37, 39 as components of the separator portion 30.

B. Modifications

The present invention is not limited to the above embodiment and modes and may be embodied in various other forms without departing from the scope of the invention.

B-1. First Modification:

While the separator portion 30 and the base portion 40 are integrally molded using a resin member, the present invention is not limited thereto. The separator portion 30 and the base portion 40 may be formed of different members. For example, the present invention may be applied to the known sensor disclosed in Japanese Laid-Open Patent Publication No. 2007-71582. That is, the present invention may be applied to a sensor including: a ceramic separator; a metal case as a base portion surrounding the separator; and an urging metal disposed between the separator and the case and supporting the separator in the axial direction.

B-2. Second Modification:

While the first and second regulation portions 37, 39 are formed of a single member (separator portion 30) in the above-mentioned embodiment, the first and second regulation portions 37, 39 may be formed of different members. Further, while the first and second regulation portions 37, 39 are portions of the separator portion 30, the first and second regulation portions 37, 39 may be formed of members separated from the separator portion 30. For example, the first and second regulation portions 37, 39 may be formed of members separated from the separator portion 30, and mounted to the separator portion 30. The second regulation portion 39 may be omitted. Preferably, the first and second regulation portions 37, 39 are made of an insulating material such as a synthesis resin. In this case, a detection signal output from the detection element 20 can be output to an external device with high accuracy.

B-3. Third Modification:

In the above-mentioned embodiment, the connection terminal 60 may not have the inward extending portion 64, 64a. That is, the spring portion 65, 65a may be directly connected to the front end portion 621 of the frame body portion 62.

B-4. Fourth Modification:

In the above-mentioned embodiment, in the assembled state, the first regulation portion 37 is in contact with the frame body portion 62 and the second regulation portion 39 is in contact with the inward extending portion 64, 64a. However, the present invention is not limited thereto. The first regulation portion 37 may face the frame body portion 62 and the second regulation portion 39 may face the inward extending portion 64, 64a. Also in this case, a movement amount (positional deviation) of the element contact portion 61, 61a along the axial direction CD in the assembled state can be reduced by the first and second regulation portions 37, 39. Preferably, the first regulation portion 37 is disposed in a range where at least the front end portion 621 of the frame body portion 62 is located. Thereby, movement of the front end portion 621 in the direction approaching the detection element 20 can be regulated by the first regulation portion 37 with higher accuracy.

B-5. Fifth Modification:

Although the sensor 200 is a gas sensor in the above-mentioned embodiment, the present invention may be applied to various sensors such as a temperature sensor and a pressure sensor. When the sensor 200 is a temperature sensor, the detection element 20 outputs a detection signal for detecting the temperature of a measurement target. When the sensor 200 is a pressure sensor, the detection element 20 outputs a detection signal for detecting the pressure of the measurement target.

The present invention is not limited to the above embodiments, modes, and modifications/variations and can be embodied in various forms without departing from the scope of the present invention. For example, it is feasible to appropriately replace or combine any of the technical features of the aspects of the present invention described in "Summary of the Invention" and the technical features of the embodiments, modes, and modifications/variations of the present invention in order to solve part or all of the above-mentioned problems or achieve part or all of the above-mentioned effects. Any of these technical features, if not explained as essential in the present specification, may be deleted as appropriate.

DESCRIPTION OF REFERENCE NUMERALS 10 terminal housing unit
15 attachment portion
16 metal shell
17 protector
18 external protector
19 internal protector
20 detection element
20fa first plate surface
20fb second plate surface
21 detection portion
22 element rear end portion
24a first metal terminal portion
24b second metal terminal portion
24c third metal terminal portion
24d fourth metal terminal portion
24e fifth metal terminal portion
28 element layer
29 heater layer
30 separator portion
31 bottom portion
34 first housing space portion
34a first housing space portion
34b second housing space portion
34c third housing space portion
34d fourth housing space portion
34e fifth housing space portion
34f sixth housing space portion 35 partition
35g chamfered portion
35p corner portion
37 first regulation portion
38 groove
39 second regulation portion
40 base portion
41 main body portion
44 side portion
50 connector portion
52 connector terminal
54 one end portion
56 other end portion
58 opening portion
60 connection terminal
60a first connection terminal
60b second connection terminal
60c third connection terminal
60d fourth connection terminal
60e fifth connection terminal
61, 61a element contact portion
62 frame body portion
63 projecting portion
64, 64a inward extending portion
65, 65a spring portion
67 terminal contact portion
68 engagement portion
69 connector contact portion
90 detection portion protection layer
157 crimp ring
158 seal member
159 seal member
162 groove portion
164 rear end portion
167 front-side circumferential portion
168 rear-side circumferential portion
169 ledge portion
171 ceramic sleeve
173 powder-charged layer
175 ceramic holder
200 sensor
411 groove
621 front end portion
624 rear end portion
641 inward end portion
O axis
CD axial direction
FD opposing direction
BS rear side
AS front side

The invention claimed is:

1. A sensor comprising:
a detection element having a first main surface, a second main surface opposed to the first main surface, a plate shape extending in an axial direction, and an electrical connection terminal portion that is formed at a rear side of the detection element in the axial direction;
a separator including an insertion portion into which the rear side of the detection element is inserted, and a plurality of terminal housing portions that are disposed surrounding a circumference of the insertion portion around the axial direction, and extend in the axial direction; and
a connection terminal that is sandwiched and held between the detection element and the separator while being inserted into at least one of the plurality of terminal housing portions, and is electrically connected to the electrical connection terminal portion to form a current path, wherein
a front side of the detection element in the axial direction is directed to a measurement target,
the connection terminal comprising:
an elongated frame body portion extending in the axial direction; and
an element contact portion that is folded back from a front end portion of the frame body portion and extends to the rear side and in a direction approaching the detection element, and is in contact with the electrical connection terminal portion, and
the sensor further comprising:
a first regulation portion provided at a position closer to the detection element relative to the frame body portion, in a direction in which the first main surface and the second main surface oppose each other, said first regulation portion regulating movement of the frame body portion in the direction approaching the detection element.

2. The sensor according to claim 1, wherein
the first regulation portion regulates the movement of the frame body portion by contacting the frame body portion in a state where the connection terminal is assembled as a component of the sensor.

3. The sensor according to claim 1, wherein
the first regulation portion is configured to regulate the movement of the frame body portion by contacting the frame body portion in an assembling process where the rear side of the detection element is disposed at the insertion portion while the connection terminal is inserted into the terminal housing portion.

4. The sensor according to claim 1, wherein
the first regulation portion is provided in the separator.

5. The sensor according to claim 1, wherein
the element contact portion includes:
an inward extending portion that is connected to the front end portion of the frame body portion, and extends from the frame body portion to a side where the detection element is located; and
a spring portion that is connected to an inward end portion of the inward extending portion, where the detection element is located, and extends in a direction away from the inward extending portion to the rear side in the axial direction, the spring portion forming a terminal contact portion to be in contact with the electrical connection terminal portion, and
the sensor further comprising a second regulation portion that is located on the rear side relative to the inward extending portion, and regulates movement of the inward extending portion to the rear side.

6. The sensor according to claim 5, wherein
the second regulation portion regulates the movement of the inward extending portion by contacting the inward extending portion in the state where the connection terminal is assembled as a component of the sensor.

7. The sensor according to claim 5, wherein
the second regulation portion is configured to regulate the movement of the inward extending portion by contacting the inward extending portion in an assembling process where the rear side of the detection element is disposed at the insertion portion while the connection terminal is inserted into the terminal housing portion.

8. The sensor according to claim 5, wherein the first regulation portion and the second regulation portion are formed of a single common member.

9. The sensor according to claim 5, wherein the second regulation portion is provided in the separator.

* * * * *